US010555677B2

(12) United States Patent
Fleischer et al.

(10) Patent No.: US 10,555,677 B2
(45) Date of Patent: Feb. 11, 2020

(54) METHOD AND DEVICE FOR IMPROVING PREDICTION AND DETECTION OF CHANGE IN A PHYSIOLOGICAL CONDITION

(71) Applicant: MEDICUS ENGINEERING APS, Aarhus N (DK)

(72) Inventors: Jesper Fleischer, Hojbjerg (DK); Simon Lebech Cichosz, Aarhus N (DK)

(73) Assignee: MEDICUS ENGINEERING APS, Aarhus N (DK)

( * ) Notice: Subject to any disclaimer, the term of this patent is extended or adjusted under 35 U.S.C. 154(b) by 55 days.

(21) Appl. No.: 14/913,894

(22) PCT Filed: Aug. 23, 2013

(86) PCT No.: PCT/IB2013/003256
§ 371 (c)(1),
(2) Date: Feb. 23, 2016

(87) PCT Pub. No.: WO2015/025187
PCT Pub. Date: Feb. 26, 2015

(65) Prior Publication Data
US 2016/0213261 A1 Jul. 28, 2016

(51) Int. Cl.
*A61B 5/0408* (2006.01)
*A61B 5/0205* (2006.01)
*A61B 5/145* (2006.01)
*A61B 5/00* (2006.01)

(52) U.S. Cl.
CPC ........ *A61B 5/0205* (2013.01); *A61B 5/14532* (2013.01); *A61B 5/7275* (2013.01); *A61B 5/742* (2013.01); *A61B 5/7405* (2013.01)

(58) Field of Classification Search
CPC ..... A61B 5/0205; A61B 5/742; A61B 5/7405; A61B 5/7267; A61B 5/7275;
(Continued)

(56) References Cited

U.S. PATENT DOCUMENTS

| 8,185,181 B2 | 5/2012 | Feldman et al. |
| 9,050,041 B2 | 6/2015 | Feldman et al. |

(Continued)

FOREIGN PATENT DOCUMENTS

| WO | 2005037092 A1 | 4/2005 |
| WO | 2008135985 A1 | 11/2008 |

(Continued)

OTHER PUBLICATIONS

FJ Gimeno-Blanes et al., "On the feasibility of tilt test outcome early prediction using ECG and pressure parameters", EURASIP Journal on Advances in Signal Processing, vol. 33, Jan. 1, 2011, pp. 1-17, XP055132750.

(Continued)

*Primary Examiner* — Rex R Holmes
(74) *Attorney, Agent, or Firm* — Dave Law Group LLC; Raj S. Dave (57) ABSTRACT

Devices, methods and systems for predicting and detecting a change in a physiological condition of a subject are disclosed. A device for detecting and predicting a change in physiological condition of a subject may include one or more processors configured to: (i) analyze changes in a heart rhythm of a subject; (ii) analyze a signal from one or more biomarkers that are associated with a physiological condition of the subject; and (iii) determine, based on the changes in the heart rhythm and the signal from the one or more biomarkers, whether there is a change in the physiological condition of the subject during a time period.

28 Claims, 4 Drawing Sheets

(58) Field of Classification Search
CPC . A61B 5/14532; A61B 5/02405; A61B 5/746;
A61M 5/1723; G06F 19/345
See application file for complete search history.

(56) References Cited

U.S. PATENT DOCUMENTS

| | | | |
|---|---|---|---|
| 2005/0115561 A1* | 6/2005 | Stahmann | A61B 5/0031 128/200.24 |
| 2005/0137470 A1* | 6/2005 | Rosenthal | A61B 5/02405 600/316 |
| 2006/0281980 A1 | 12/2006 | Randlov et al. | |
| 2010/0030092 A1* | 2/2010 | Kristensen | A61B 5/02055 600/509 |
| 2012/0165639 A1* | 6/2012 | Engelhardt | G16H 40/40 600/365 |

FOREIGN PATENT DOCUMENTS

| | | |
|---|---|---|
| WO | 2009138976 A2 | 11/2009 |
| WO | 2010134068 A1 | 11/2010 |

OTHER PUBLICATIONS

International Search Report and Written Opinion dated Aug. 11, 2014 in International Application PCT/IB2013/003256.
Mostefa Mesbah et al., "Automatic Seizure Detection Based on the Combination of Newborn Multi-Channel EEG and HRV Information", EURASIP Journal on Advances in Signal Processing, vol. 215 Jan. 1, 2012 pp. 1-14, XP055132749.

* cited by examiner

METHOD AND DEVICE FOR IMPROVING PREDICTION AND DETECTION OF CHANGE IN A PHYSIOLOGICAL CONDITION

TECHNICAL FIELD

This disclosure relates generally to monitoring and prediction of changes in physiological conditions of a subject, and in particular, to a method and apparatus for estimating the changes that may lead to adverse effects.

BACKGROUND ART

Autonomic nervous system (ANS) is a multifunctional system regulated by the sympathetic nervous system and the parasympathetic system, providing a rapidly responding mechanism to control a wide range of bodily functions such as, for example, cardiovascular, respiratory, gastrointestinal, genitor-urinary, exocrine and endocrine secretions, and microcirculation. Furthermore, ANS is involved in the regulation of immune and inflammatory processes. Autonomic dysfunction may affect both the sympathetic nervous system and the parasympathetic nervous system and may affect any organ that is innervated by the autonomic nervous system.

Heart rate (HR) and heart rate variability (HRV) are affected by both internal and external changes in, for example, breathing, blood pressure, hormone status, mental condition and physical conditions. A number of pathophysiological conditions may shift the balance in the ANS thereby decreasing or increasing stimulation to heart's sinoatrial node which controls HR and HRV. For example, increase in blood pressure causes arteries to stretch, thereby causing increase in baroreceptor discharge frequency which, in turn, causes increase in parasympathetic and decrease in sympathetic activity. Similarly, carotid chemoreceptor stimulation by noradrenalin leads to slowing HR and increase in rate and depth of respiration.

SUMMARY

In an embodiment, a device may include one or more processors configured to: (i) analyze changes in a heart rhythm of a subject; (ii) analyze a signal from one or more biomarkers that are associated with a physiological condition of the subject; and (iii) determine, based on the changes in the heart rhythm and the signal from the one or more biomarkers, whether there is a change in the physiological condition of the subject during a time period.

In an embodiment, a method for predicting and/or detecting a change in a physiological condition of a subject is disclosed. The method may include analyzing changes in a heart rhythm of a subject; analyzing a signal from one or more biomarkers that are associated with a physiological condition of the subject; and determining, based on the changes in the heart rhythm and the signal from the one or more biomarkers, whether there is a change in the physiological condition of the subject during a time period.

In an embodiment, a system for predicting and/or detecting a change in a physiological condition of a subject is disclosed. The, the system may include a device comprising one or more processors configured to (a) analyze changes in a heart rhythm of a subject; (b) analyze a signal from one or more biomarkers that are associated with a physiological condition of the subject; and (c) determine, based on the changes in the heart rhythm and the signal from the one or more biomarkers, whether there is a change in the physi ological condition of the subject during a time period; one or more sensors configured to measure the heart rhythm of the subject; and one or more sensors configured to measure the signal.

BRIEF DESCRIPTION OF DRAWINGS

In the present disclosure, reference is made to the accompanying drawings, which form a part hereof. In the drawings, similar symbols typically identify similar components, unless context dictates otherwise. Various embodiments described in the detailed description, drawings, and claims are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein.

DETAILED DESCRIPTION

Before the present methods and systems are described, it is to be understood that this disclosure is not limited to the particular processes, methods and devices described herein, as these may vary. It is also to be understood that the terminology used herein is for the purpose of describing the particular versions or embodiments only, and is not intended to limit the scope of the present disclosure which will be limited only by the appended claims. Unless otherwise defined, all technical and scientific terms used herein have the same meanings as commonly understood by one of ordinary skill in the art.

It must also be noted that as used herein and in the appended claims, the singular forms "a", "an", and "the" include plural reference unless the context clearly dictates otherwise. Thus, for example, reference to a "biomarker" is a reference to one or more biomarkers and equivalents thereof known to those skilled in the art, and so forth. Nothing in this disclosure is to be construed as an admission that the embodiments described in this disclosure are not entitled to antedate such disclosure by virtue of prior invention. As used in this document, the term "comprising" means "including, but not limited to."

As used herein, the term "biomarker", interchangeably used with the term "biological marker", refers to an objectively measurable indicator of a biological state. Biomarkers may be used as indicators of, for example, biological processes, pathogenic processes, pharmacologic responses to a therapeutic intervention. Examples of biomarkers include, but are not limited to, heart rate, heart rate variability, electrical activity in an organ such as brain, heart or a muscle, electrooculogram, sudomotor function, breathing rate, partial oxygen pressure, blood pressure, blood glucose levels, blood alcohol levels, presence or absence of proteins in blood and/or cells, bioimpedance, galvanic skill response, nerve conduction, pulse wave measurement, pulse wave velocity, magnetic resonance imaging (MRI), motion detection and/or analysis, rates of absorption, distribution, metabolism and/or elimination of a chemical, radioactive or biochemical substance in the body, and so forth. In some instances a surrogate for a biomarker may be used as a measurable indicator of a biological state. For example, Continuous Glucose Monitor (CGM) is a surrogate measure for blood glucose measurement. CGM devices measure the glucose level of interstitial fluid and is be calibrated with a traditional blood glucose measurement. Typically, glucose levels in interstitial fluid lag behind blood glucose values.

In various embodiments, biomarker measurements may be obtained periodically. For example, blood glucose values may be obtained every 5 minutes, or every 10 minutes, and so forth. Periodicity of measurement of biomarker data may vary for different biomarkers and may depend on factors such as, for example, typical frequency of biomarker measurement may be once every 1 second, once every 30 seconds, once every 1 minute, once every 5 minutes, once every 10 minutes, once every 30 minutes, once every 1 hour, or any frequency between any two of these frequencies.

A processor refers to a machine for data processing. For example, the processor could be a microprocessor chip.

A physiological condition refers to the condition or state of the body or bodily functions. For example, a physiological condition could be a condition characteristic of or appropriate to an organism's healthy or normal functioning.

Biomarkers may be used to make a clinical determination of a physiological condition, which includes a pathophysiological condition and may be used alone or in conjunction with other biomarkers or indicators (e.g., a patient's medical history) and symptoms. A change in a measurement of a biomarker or a surrogate of a biomarker may have physiological significance, i.e., a characteristic of or appropriate to an organism's healthy or normal functioning. For example, a drop in blood glucose level may indicate onset of hypoglycemia which may, in certain cases, require clinical intervention.

As used herein, "heart rate variability" (HRV) refers to variation in the time interval between heartbeats. HRV has been found to be a measure of the balance in the autonomic nervous system and is dependent on both internal and external changes in the body. Decreased parasympathetic nervous system activity or increased sympathetic nervous system activity results in reduced HRV. HRV may be measured using, for example, electrocardiogram, blood pressure, ballistocardiograms, pulse wave signals derived from photoplethysmograph, and so forth. In various embodiments, HRV may be measured at different sampling rates such as, for example, 0.01 Hz, 0.05 Hz, 0.1 Hz, 0.5 Hz, 1 Hz, 5 Hz, 10 Hz, 50 Hz, 100 Hz, 500 Hz, 1 kHz, and so forth or at any sampling rate between any two of these sampling rates.

By combining the complex dynamic/pattern of HRV with a surrogate measure of a biomarker it may be possible to improve the detection and prediction of a given change in a physiological condition which is measured by the biomarker surrogate. The HRV dynamic/pattern adds important information regarding the modulation of the autonomic nervous system and thereby can be used to clarify whether a change or event measured by the biomarker is of physiological significance, which could include a change or event of clinical interest that might require clinical intervention. This clarification is more significant when using a surrogate measure of a biomarker. For example, when the biomarker surrogate is CGM, there is a lag-time between CGM measurements and actual blood glucose levels (glucose levels in interstitial fluid lag behind blood glucose values) causing poor accuracy in event detection. Therefore, in terms of detection of hypoglycemia, CGM devices, have poor specificity and thus result in numerous false positive alerts. By combining pattern recognition of HRV with a CGM device the detection and prediction of hypoglycemia may be significantly improved. Besides detection and prediction of hypoglycemia the methods disclosed herein may be used in any biomarker surrogates that are influenced by the autonomic nervous system.

Disclosed herein are methods for monitoring and predicting changes in physiological conditions using changes in heart rate and heart variability in conjunction with one or more suitable biomarkers. Embodiments disclosed herein also describe devices and systems for implementing those methods and methods of use of such devices and systems. In various embodiments, devices and systems described herein may be used as part of other systems for prophylaxis, or treatment and/or alleviation of symptoms of a disease or a physiological condition.

Figure 1:
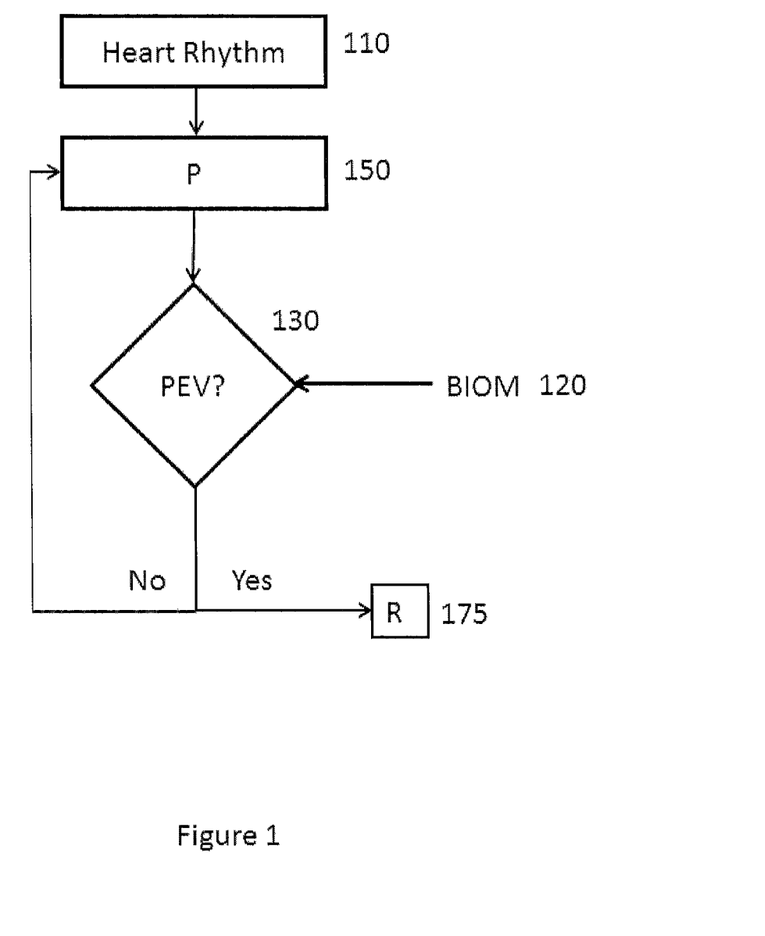
FIG. 1 depicts an illustrative process for a method of monitoring and predicting a change in a physiological condition using Heart Rate Variability (HRV) in combination with one or more biomarkers according to an embodiment.

FIG. 1 depicts an illustrative process for a method of monitoring and predicting a change in a physiological condition using Heart Rate Variability (HRV) in combination with one or more biomarkers according to an embodiment. At block 110, HRV of a subject is measured by a sensor. The HRV data fed to a processor P which, at block 150, analyzes the HRV data based on a pre-determined algorithm. At block 130, processed HRV data is combined (using, e.g., another processor not shown in FIG. 1) with measurements relating to one or more biomarkers BIOM from one or more sensors gathered at block 120 and analyzed for change in a physiological condition. This analysis may be fed back to processor P for analysis at block 150. If the change in the physiological condition is deemed, based on a pre-determined set of criteria, a reaction R is provided at block 175.

In various embodiments, the patterns in the HRV data may be used to evaluate the clinical relevance of each data point obtained from the biomarker measurements. For example, in an embodiment, glucose measurement is used for detection of hypoglycemia. In such embodiment, glucose levels are measured periodically (e.g., every 5 minutes) and patterns in HRV data are used to determine whether a particular glucose measurement indicates an onset of hypoglycemia. In other embodiments, other biomarkers may be used and measurements obtained at a different frequency. In some embodiments, the biomarker data may undergo processing similar to the HRV data.

In various embodiments, physiological conditions may be induced under controlled clinical conditions while gathering HRV data. In many embodiments, HRV data may be gathered for up to 10 hours prior to induction of the physiological event and up to 10 hours after the induction of the physiological event. As such, incidence of various features and patterns extracted from the HRV data may be correlated with the particular physiological event being induced based on the analysis being performed.

Figure 2:
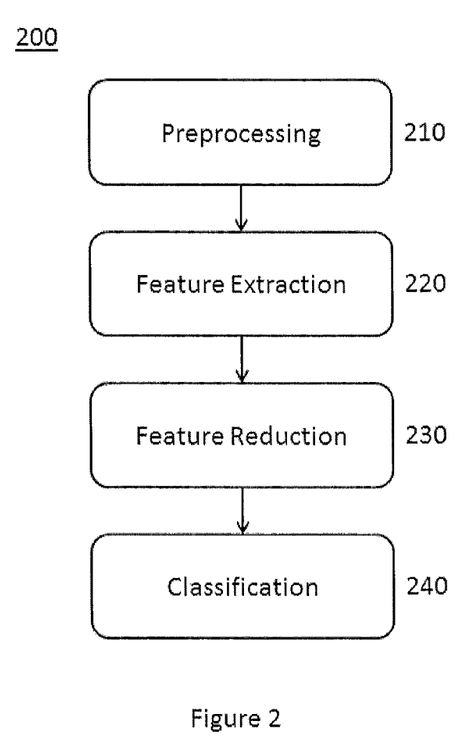
FIG. 2 depicts an illustrative pattern recognition model according to an embodiment.

HRV of a subject may be measured using any device or method. For example, in an embodiment, HRV of a subject is measured using electrocardiogram (ECG). FIG. 2 depicts an illustrative pattern recognition model according to an embodiment. In various embodiments, analysis of HRV at block 150 may include, for example, preprocessing at block 210, feature extraction at block 220, feature reduction at block 230, and classification at block 240.

In embodiments where HRV is measured using ECG, a signal from the ECG is preprocessed, at block 210, for detection of peaks and calculation of RR-intervals. RR-interval, as used herein, is the interval between an R wave and the next R wave as measured by the ECG. In various embodiments, RR-intervals may be divided in epochs of several minutes. It will be understood by one skilled in the art that any time length of an epoch may be chosen and will depend on factors such as, for example, data sampling rate, processing power, memory available to the processor, efficiency of algorithms used for analysis, and so forth. In an embodiment, for example, duration of an epoch may be 5 minutes.

RR-interval outliers from each epoch may then be replaced with a mean from that particular epoch. Outliers, in some embodiments, may be defined as RR-intervals deviating 50% from previous data RR-interval or outside 3 standard deviations. Epochs may be analyzed using proprietary or commercially available tools. The analysis may be performed using one or more of analysis tools such as, for example, of Poincare Plots, Nonlinear analysis, time-frequency analysis and performed in time domain or frequency domain. Power spectra density may then be estimated using parametric or non-parametric models such as, for example, Welch's method, auto regression, periodogram, Bartlett's method, autoregressive moving average, maximum entropy, least-squares spectral analysis, and so forth.

Preprocessing of the ECG signal may be followed by feature extraction, at block 220. Preprocessed RR-interval data is sent to block 220 to find, preferably, a small number of features that are particularly distinguishing and/or informative for classification of the features based on physiological conditions being induced. In various embodiments, features extracted, at block 220, from the RR-interval data up to several epochs prior to the physiological event may be used for calculating various features. In some embodiments, analysis may be performed on data, for example, 10 epochs, 15 epochs, 20 epochs, 30 epochs, 40 epochs, 50 epochs, 100 epochs or any number of epochs therebetween, prior to the physiological event.

Analysis performed on the RR-interval data at block 220 may, in various embodiments, include, for example, differentiation, averaging, calculation of slope, ratios of instantaneous values, standard deviation, skewness, regression coefficients, slopes of regression ratios, and standardized moment, and so forth. Features extracted from the HRV data may include, for example, median heart rate average from particular epoch range prior to an event, or the skewness of standard deviation of normal-to-normal intervals from particular epoch range prior to an event, and so forth.

RR-interval data extracted at block 220 may include a large number of different features may be evaluated for their ability to discriminate for a physiological event. Such features may then, be passed down to block 230 to be grouped to form patterns that may be indicative of a particular physiological event. At block 230, a ranking algorithm based on e.g. a t-test may be used, in some embodiments, for eliminating features that do not signify an event.

In some embodiments, the ranking algorithm may calculate an average separability criterion for each feature. Such a criterion may reflect the ability of the classification method to separate the means of any two classes of features in relation to the variance of each class. Subsequently, various features may be correlated with physiological events. Features with lowest separability may be eliminated if correlation with higher ranking features exceeds a threshold. In an embodiment, a correlation threshold of, for example, 0.7 may be used. In various embodiments, the correlation threshold may be chosen depending on the desired specificity and sensitivity of prediction of the physiological event. In many embodiments, cross-validation may be performed to reduce generalization errors.

Once the features are extracted and reduced, particular features may be chosen for their ability to predict a physiological event based on correlation factors. This is followed by classification, at block 240, of the features to correlate them with particular physiological events. Various classification models may then be used for classifying physiological events as normal or abnormal based on such features. For example, in an embodiment, non-probabilistic binary linear classifier support vector machine may be used. A skilled artisan will appreciate that other classification methods may be also used, alone or in combination. For example, linear classifier models such as Fisher's linear discriminant, logistic regression, naive Bayes classifier, Perceptron, may be used for classification. Other examples of classification models include, but are not limited to, quadratic classifiers, k-nearest neighbor kernel estimation, random forests decision trees, neural networks, Bayesian networks, Hidden Markov models, Gaussian mixture models, and so forth. In some embodiments, multi-class classification may also be used, if needed.

In an embodiment, at block 240, forward selection may be used to select a subset of features for optimal classification. This selection may be performed by including a cross-validation with, for example, 10 groups and allocating a particular number of events for training the model. Forward selection may start with no features followed by assessing each feature to find the best feature that correlates with the particular physiological event. Such feature may, then, be included in an optimal feature subset for appropriate classification. Selection of new features may be repeated until addition of new features does not result in improved predictive performance of the model.

Figure 3:
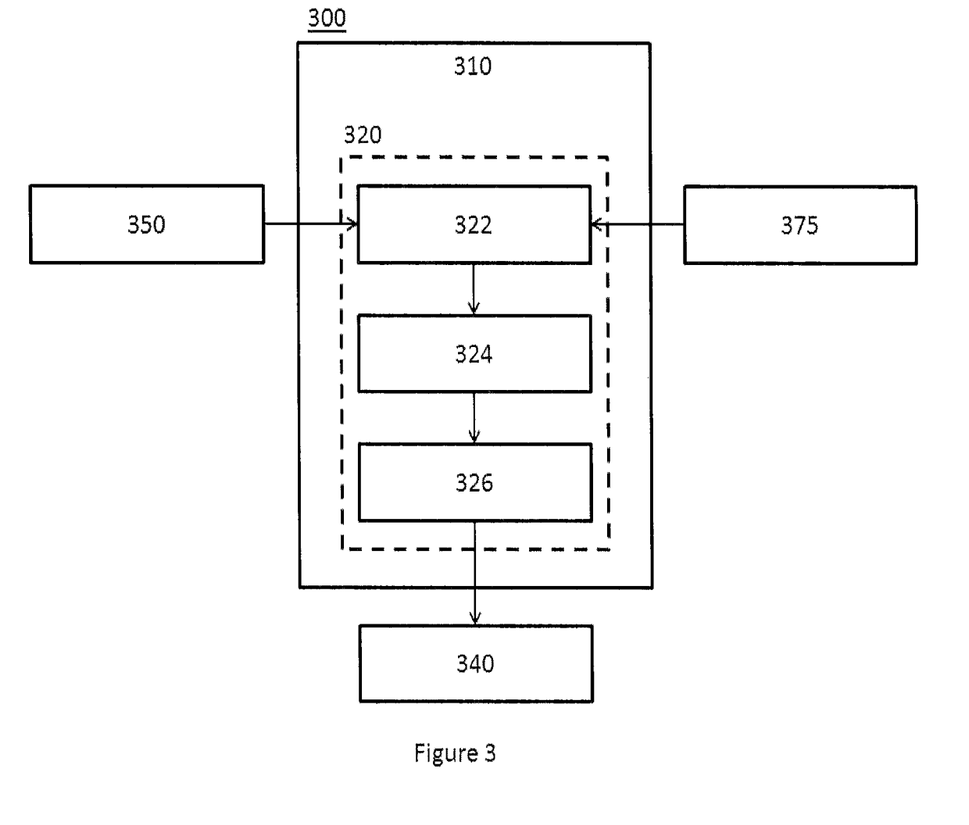
FIG. 3 depicts a block diagram of a device used for analysis of HRV data in accordance with various aspects and principles of the present disclosure.

FIG. 3 depicts a block diagram of a device used for analysis of HRV data in accordance with various aspects and principles of the present disclosure. Device 300 used for analysis of HRV data may include processor 310 configured to run algorithm 320 that enables prediction or detection of a physiological event. Heart rhythm 350 along with at least one biomarker 375 and their time of measurement are received and analyzed by algorithm 320. In some embodiments, measurements of heart rhythm 350 and biomarker 375 may be entered manually. In other embodiments, the measurements may be transmitted automatically to processor 310 using a wired or a wireless connection to device 300. Algorithm 320 may include, calculating one or more statistical measures, at block 322, of heart rhythm 350 and biomarker 375 data. At block 324, the physiological state or change in the physiological state is estimated and analyzed for a possibility that the physiological state or change in the physiological state may be non-healthy. At block 326, an output is generated based on the analysis of block 324. For example, if it is determined, at block 324, that a change in physiological state is non-healthy, an alarm signal is generated at block 326. Device 300 may produce a reaction 340 based on the output generated at block 326. In various embodiments, reaction 340 may be a visual, audio, or audiovisual signal such as, for example, an alarm, a text message, a flashing light, and so forth.

In many embodiments, processor 310 may be part of a computer, a tablet, a smartphone, or a standalone device. In some embodiments, the device may have in-built sensors for measuring HRV data 350. For example, a smartphone having a light emitting diode (LED) capable of producing infra-red light and an optical sensor (e.g., a camera) may be able to obtain HRV data using IR thermography. In many embodiments, the device used for analyzing the HRV data may include, for example, a controlling unit (e.g., a digital signal processor or DSP), a memory (e.g., random access memory, and/or non-volatile memory), one or more sensors (e.g., IR sensors, electrodes, etc.), one or more feedback mechanisms (e.g., display, a printer, speakers, LEDs or other light sources, etc.), and/or one or more input ports. The device for analyzing HRV data may also include sensors for measuring and analyzing any other biomarker(s).

In an embodiment, HRV measurements 350 may be combined, at block 322, with measurements of blood glucose levels 375 for monitoring and prediction of hypoglycemia. In such embodiments, HRV data 350 may be combined with, e.g., blood glucose measurements 375 taken over a period of time prior to a hypoglycemic event. Patterns from the combination of HRV and blood glucose data may be used to discriminate between normoglycemia and hypoglycemia. A model may be trained by analyzing HRV features over, e.g., 10-20 epochs combined with blood glucose measurements prior to an induced hypoglycemic event. Once trained to discriminate between normoglycemic events and hypoglycemic events, the model may then be used to predict, at block 324, the occurrence of a hypoglycemic event based on HRV and blood glucose measurements.

Blood glucose data 375 may be obtained intermittently or continuously. In some embodiments, it may be possible to obtain blood glucose data using non-invasive technologies that include, for example, infra-red detection, ultrasound or dielectric spectroscopy and so forth. In many embodiments, such technologies may be integrated with equipment used for obtaining HRV data. In other embodiments, an implanted chip may be used for obtaining continuous blood glucose data.

Table 1 provides a list of biomarkers that may be used in concert with HRV for predicting and monitoring various physiological conditions.

TABLE 1

List of biomarkers or biomarker surrogates used for detection/prediction for physiological events/conditions (EEG—electroencephalogram; EMG—Electromyography; ECG—Electrocardiography).

| Physiological condition | Biomarker or surrogate measure of a biomarker |
|---|---|
| Epileptic attack | EEG, EMG, motion detection |
| Asthma attack | EEG, breathing (sounds and rate) |
| Panic attack | EEG, ECG, breathing (sounds and rate), sudomotor function |
| Heart attack or event | ECG, pulse wave velocity |
| Sudden hypotension | Blood pressure |
| Sleep apnea | EEG, breathing (sounds and rate) |
| Fatigue | ECG, EMG, motion detection |
| Stress, including post-traumatic stress | EEG, bioimpedance, breathing (sounds and rate) |
| Neuropathy | Bioimpedance, nerve conduction, EEG, EMG, dolorimeter, vibration testing, motion detection |
| Dehydration | Blood pressure, bioimpedance, breathing |
| Liveness detection | Bioimpedance |
| Lie detection | Polygraph |

Another embodiment is implemented as a program product for implementing systems and methods described herein. Some embodiments can take the form of an entirely hardware embodiment, an entirely software embodiment, or an embodiment containing both hardware and software elements. One embodiment is implemented in software, which includes but is not limited to firmware, resident software, microcode, etc.

Furthermore, embodiments can take the form of a computer program product (or machine-accessible product) accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device). Examples of a computer-readable medium include a semiconductor or solid-state memory, magnetic tape, a removable computer diskette, a random access memory (RAM), a read-only memory (ROM), a rigid magnetic disk, and an optical disk. Current examples of optical disks include compact disk—read only memory (CD-ROM), compact disk—read/write (CD-R/W), and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

The logic as described above may be part of the design for an integrated circuit chip. The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication.

The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product.

The foregoing detailed description has set forth various embodiments of the devices and/or processes by the use of diagrams, flowcharts, and/or examples. Insofar as such diagrams, flowcharts, and/or examples contain one or more functions and/or operations, it will be understood by those within the art that each function and/or operation within such diagrams, flowcharts, or examples can be implemented, individually and/or collectively, by a wide range of hardware, software, firmware, or virtually any combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

EXAMPLES

Embodiments illustrating the devices, methods and systems described herein may be further understood by reference to the following non-limiting examples:

Patients with type-1 diabetes following a strict glycemic control are disposed to suffer severe hypoglycemia.
Detection of Hypoglycemia Based on Heart Rate Variability and CGM Data Embodiments described in the examples may utilize the devices, methods and processes described herein with respect FIGS. 1-3.
Data Collection:

Data from 10 patients was obtained. 10 adults with type I diabetes were recruited for studies into hypoglycemia under clinical settings. None of the patients with diabetes had a history of cardiovascular disease. None of the patients were taking drugs affecting the cardiovascular system, and all had normal electrocardiograms.

On the study day, hypoglycemia was induced by a single subcutaneous bolus of insulin aspart. Subjects were placed in a hospital bed with the back rest elevated to a comfortable position. Equipment for measuring the ECG (lead II) and a CGM device (Guardian RT, Minimed, Inc., Northridge, Calif.) producing a reading every 5 minutes were mounted and an intravenous cannula was placed in an antecubital vein in both forearms. Blood samples for measurements of insulin were taken at the beginning and end of a baseline period. Throughout the experiment, blood glucose measurements were obtained frequently from earlobe capillary blood.

Blood glucose readings were spline resampled with a rate of 5 minutes equivalent to each reading of the CGM device. The blood glucose readings were used as reference for periods/events with hypoglycemia and categorize events as (i) hypoglycemia—defined as the point of time of a blood sample closest to the value of 3 mmol/l glucose, and normoglycemia—defined as the point of time of a blood sample approximately 1 hour prior to the hypoglycemic event.

Once the HRV and blood glucose data is collected, all data processing was performed using custom analysis software developed in MATLAB R2011b (Mathworks, Natick, Mass.).
Preprocessing:

The ECG V5 signal was used for detection of peaks and calculation of RR-intervals. RR-intervals were divided in epochs of 5 minutes during the trial. RR-interval outliers from each epoch were replaced with the mean from that particular epoch. Outliers were defined as RR-intervals deviating 50% from previous data RR-interval or outside 3 standard deviations.

Epochs were analyzed using HRV analysis software (HR-VAS) module and 103 measures ranging from time domain, Poincare, Nonlinear, time-frequency to frequency domain were derived from the epoch. Two different models were used to estimate power spectra density: welch and auto regression.
Feature Extraction and Reduction:

In short, feature extraction and reduction is performed to find preferably small number of features that are particularly distinguishing or informative for the classification. Measures derived from RR-interval epochs 10-40 prior to an event were used for calculating multiple features. Table 2 shows calculations used to combine different epoch measures.

TABLE 2

List of equations used to combine HRV measures into features. $M_y$ represent a HRV measure y, $epc_{x1}$ represent an 5 minutes RR-interval epoch, $\mu$ is the arithmetic mean, $\alpha$ is the slope regression coefficients, $\sigma$ is the standard deviation, $\gamma 1$ is the third standardized moment.

| Description | Equation |
| --- | --- |
| Differentiation | $M_y epc_{x1} - M_y epc_{x2}$ |
| Averaging | $\mu (M_y epc_{x1} \ldots M_y epc_{xn})$ |
| Slope | $\alpha (M_y epc_{x1} \ldots M_y epc_{xn})$ |
| Standard deviation | $\sigma (M_y epc_{x1} \ldots M_y epc_{xn})$ |
| Skewness | $\gamma_1 (M_y epc_{x1} \ldots M_y epc_{xn})$ |
| Ratio | $M_y epc_{x1} / M_y epc_{x2}$ |

Example of features could be (a) the median heart rate averaged from epochs 10-20 prior to an event or (b) the skewness of standard deviation of Normal-to-Normal intervals (SDNN) from epochs 10-40 prior to an event.

To classify the patterns, 3296 different features were evaluated for their discrimination abilities. A ranking algorithm based upon a t-test was used to eliminate features.

The ranking algorithm calculates an average separability criterion for each feature, which is the ability to separate the means of the two classes in relation to the variance of each class. The features are then correlated, and the feature with the lowest separability criteria is eliminated if correlation with higher ranking features exceeds the threshold. In this study a correlation threshold of 0.7 was used. To ensure that the features obtained would not be over fitted, i.e. to reach a low generalization error, a cross-validation method was used. A total of the best 20 features were used to inclusion in the classification model.

Classification Model:

Non-probabilistic binary linear classifier Support vector machines (SVM) was used to classify the events of normoglycemia and the events of hypoglycemia. First a forward selection method was used to select a subset of features for the optimal classification model. This selection was done including a cross-validation with ten groups, leaving 2 events out for classification and 18 events for training. Forward selection starts with no features and assesses every single feature and finds the best feature. This feature is then included as part of the optimal feature subset. All other features are added again to form a two-feature subset etc. this is repeated until new features doesn't increase the performance.

A subset of features selected is then used for the final classification model, which also included a ten-fold cross-validation. Sensitivity and specificity is used to evaluate the classification model.

Figure 4:
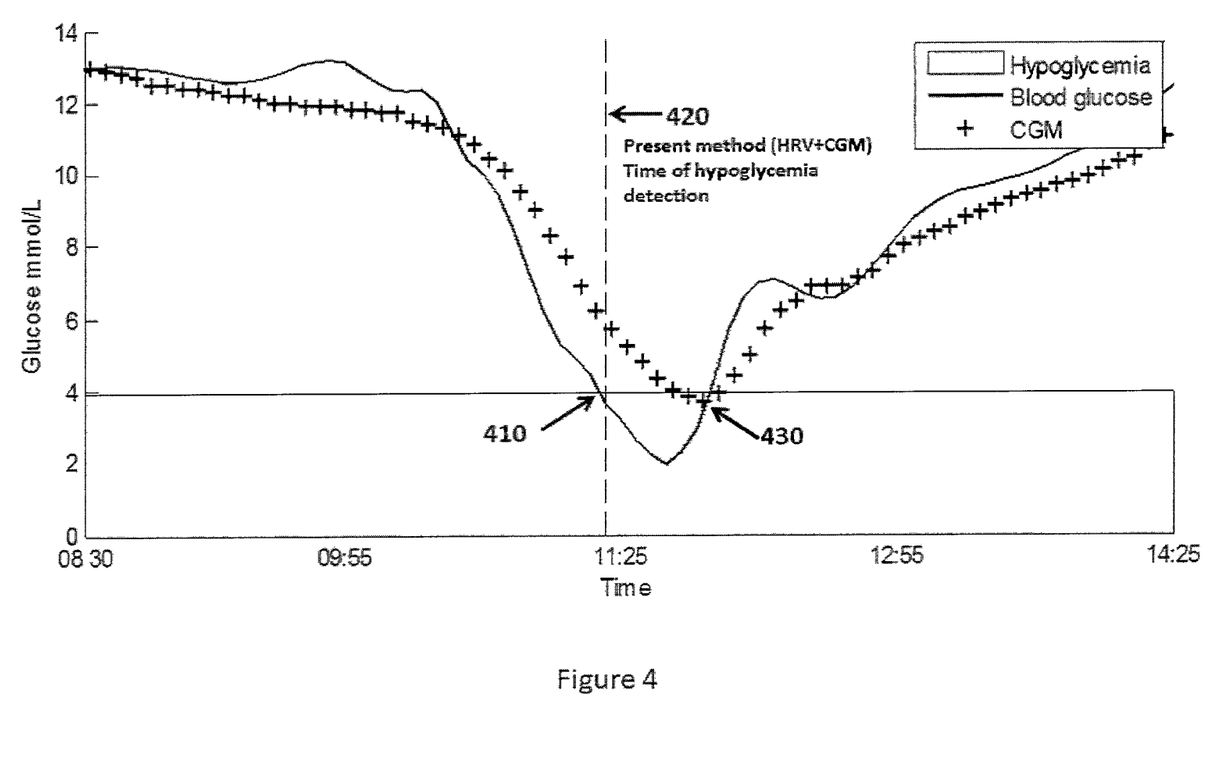
FIG. 4 shows an example of detection of hypoglycemia based on HRV data and data from a Continuous Glucose Monitor (CGM) for a subject, according to an embodiment.

Results:

A total of 903 samples equivalent to 4515 minutes among 10 patients with 16 hypoglycemic events were analyzed and classified using the model. The sample-based evaluation yielded a ROC AUC of 0.98. With a specificity of 99% the model had a sensitivity of 79%. This is a significant improvement over CGM alone. Event-based, the model classified all hypoglycemic events correctly, did not detect any false-positive events and had a lead-time of 22±(12) minutes. CGM alone was able to detect 12 out of 16 events with a lead-time 0±(11) minutes. FIG. 4 shows the data for one patient where CGM alone detects hypoglycemia, indicated by 430, late after the real onset, indicated by 410, while the present method detects the hypoglycemic event, indicated by 420, one minute after the real onset.

The invention claimed is:

1. A device comprising one or more processors configured to:
   obtain continuously over time, via one or more sensors, both a heart rhythm signal related to a heart rhythm of a subject and an interstitial fluid glucose level signal related to a glucose level of an interstitial fluid of the subject;
   analyze continuously over time changes in a pattern of a heart rate variability of the subject based on the heart rhythm signal;
   analyze continuously over time changes in the glucose level of the interstitial fluid based on the interstitial fluid glucose level signal;
   extract features from the pattern of the heart rate variability and the glucose level of the interstitial fluid;
   reduce the features extracted based on a ranking algorithm to eliminate certain features that do not signify a physiological event;
   combine the pattern of the heart rate variability and the interstitial fluid glucose level signal; and
   predict, for a physiological condition during a future time period of the subject for which the glucose level of the interstitial fluid is surrogate measurement, whether there would be a change in the physiological condition of the subject during the future time period, a prediction being based on the correlated changes in the pattern of the heart rate variability and the changes in the glucose level of the interstitial fluid, wherein a continuous glucose monitor is a surrogate measure for blood glucose measurement.

2. A device of claim 1, wherein the one or more processors are configured to process and correlate data related to the changes in the pattern of the heart rate variability to determine whether a rhythm signal or a change in the heart rhythm signal is of a physiological significance.

3. A device of claim 1, further comprising at least one of the one or more sensors configured to obtain the heart rhythm signal or the interstitial fluid glucose level signal.

4. A device of claim 1, wherein the one or more processors are configured to predict whether there is a change in the physiological condition of the subject based on (i) the changes in the pattern of the heart rate variability, (ii) the changes in the glucose level of the interstitial fluid and (iii) a pattern recognition model trained using prior heart rhythm measurements of the subject and prior glucose level measurement of the subject.

5. A device of claim 1, wherein the one or more processors are further configured using classification models in pattern recognition to determine whether the changes in the pattern of the heart rate variability of the subject are treated as a non-healthy incidence.

6. The device of claim 1, wherein a surrogate measurement signal includes one or more of body temperature, a heart rate or sound, a breathing rate or sound, a partial oxygen pressure, a glucose level, a blood pressure, a bioimpedance, a galvanic skin response, a motion detection signal, an electrooculogram signal, an electrocardiogram signal, a pulse wave velocity signal, a pulse wave measurement signal, a nerve conduction velocity signal, an electroencephalogram signal, an electromyogram signal, a dolorimeter measurement signal, or concentration of one or more chemicals in blood.

7. The device of claim 1, wherein the interstitial fluid glucose level signal is periodically obtained via the one or more sensors.

8. The device of claim 1, wherein the one or more processors are further configured to analyze a motion of the subject using audio or visual guidance, and wherein the one or more processors are configured to predict the physiological condition of the subject further based on an analysis of the motion of the subject.

9. The device of claim 1, further comprising a feedback mechanism for providing an audio, visual, or audio-visual feedback to the subject when a non-healthy physiological change is detected.

10. The device of claim 1, wherein the one or more processors are configured to analyze changes in the pattern of the heart rate variability by detecting patterns or changes in patterns of the heart rhythm in the heart rhythm signal using a pattern recognition method.

11. The device of claim 1, wherein a surrogate measurement signal relates to a blood glucose level.

12. A method comprising:
    obtaining continuously over time, via one or more sensors, both a heart rhythm signal related to a heart rhythm of a subject and an interstitial fluid glucose level signal related to a glucose level of an interstitial fluid of the subject;
    analyzing continuously over time, via one or more processors, changes in a dynamic pattern of a heart rate variability of the subject based on the heart rhythm signal;

analyzing continuously over time, via one or more processors, changes in the glucose level of the interstitial fluid based on the interstitial fluid glucose level signal;

extracting features from the dynamic pattern of the heart rate variability and the glucose level of the interstitial fluid;

combining the dynamic pattern of the heart rate variability and the interstitial fluid glucose level signal;

extracting features based on a ranking algorithm to eliminate a lag-time between a continuous glucose monitor measurement and an actual blood glucose level; and predicting, via the one or more processors, for a physiological condition during a future time period of the subject for which the glucose level of the interstitial fluid is a surrogate measurement, whether there would be a change in the physiological condition of the subject during the future time period, a prediction being based on the correlated changes in the complex dynamic/pattern of heart rate variability and the changes in the glucose level of the interstitial fluid, wherein a continuous glucose monitor is a surrogate measure for blood glucose measurement.

13. The method of claim 12, further comprising determining whether the changes in the pattern of the heart rate variability of the subject are to be treated as a non-healthy incidence using classifications models in pattern recognition.

14. The method of claim 12, wherein a surrogate measurement signal includes one or more of body temperature, a heart rate or sound, a breathing rate or sound, a partial oxygen pressure, a glucose level, a blood pressure, a bioimpedance, a galvanic skin response, a motion detection signal, an electrooculogram signal, an electrocardiogram signal, a pulse wave velocity signal, a pulse wave measurement signal, a nerve conduction velocity signal, an electroencephalogram signal, an electromyogram signal, a dolorimeter measurement signal, or concentration of one or more chemicals in blood.

15. The method of claim 12, wherein a surrogate measurement signal is periodically obtained via the one or more sensors.

16. The method of claim 12, wherein analyzing changes in the pattern of the heart rate variability of the subject comprises detecting patterns or changes in patterns of the heart rhythm of the subject in the heart rhythm signal using a pattern recognition method.

17. The method of claim 16, further comprising correlating patterns or changes in patterns of the heart rhythm of the subject with non-healthy instances of the physiological condition using a pattern recognition method.

18. The method of claim 12, wherein a surrogate measurement signal comprises a blood glucose level.

19. A system comprising:
one or more sensors configured to obtain continuously over time a heart rhythm signal related to a heart rhythm of a subject and to obtain continuously over time an interstitial fluid glucose level signal related to a glucose level of an interstitial fluid of the subject;
a device comprising one or more processors configured to:
obtain continuously over time, via the one or more sensors, a pattern of a heart rhythm signal and the interstitial fluid glucose level signal;
analyze continuously over time changes in a pattern of a heart rate variability of the subject based on the heart rhythm signal;
analyze continuously over time changes in the glucose level of the interstitial fluid based on the interstitial fluid glucose level signal;
combine the pattern of the heart rate variability and the interstitial fluid glucose level signal; and
predict, for a physiological condition during a future time period of the subject for which the glucose level of the interstitial fluid is a surrogate measurement, weather there would be a change in the physiological condition of the subject during the future time period, a prediction being based on the correlated changes in the pattern of the heart rate variability and the changes in the glucose level of the interstitial fluid,
wherein a continuous glucose monitor is a surrogate measure for blood glucose measurement.

20. The system of claim 19, further comprising a feedback mechanism for providing an audio, visual, or audio-visual feedback to a subject when a non-healthy physiological change is detected.

21. The system of claim 19, wherein the one or more processors are further configured using classification models in pattern recognition to predict whether the changes in the pattern of the heart rate variability of the subject are to be treated as a non-healthy incidence.

22. The system of claim 19, wherein a surrogate measurement signal includes one or more of body temperature, a heart rate or sound, a breathing rate or sound, a partial oxygen pressure, a glucose level, a blood pressure, a bioimpedance, a galvanic skin response, a motion detection signal, an electrooculogram signal, an electrocardiogram signal, a pulse wave velocity signal, a pulse wave measurement signal, a nerve conduction velocity signal, an electroencephalogram signal, an electromyogram signal, a dolorimeter measurement signal, or concentration of one or more chemicals in blood.

23. The system of claim 22, wherein the surrogate measurement signal comprises a blood glucose level.

24. The system of claim 19, wherein a surrogate measurement signal is periodically obtained via the one or more sensors.

25. The system of claim 19, wherein the one or more processors are configured to analyze the changes in the pattern of the heart rate variability by detecting patterns or changes in patterns of the heart rhythm in the heart rhythm signal using a pattern recognition method.

26. A computer program comprising a computer-readable medium having computer program logic recorded thereon arranged to execute the method of claim 12.

27. A computer-readable medium comprising computer-readable code physically embodied thereon which, when executed by a processor, causes the processor to perform a method of claim 12.

28. The method of claim 12, wherein the one or more processors are configured to predict whether there is a change in the physiological condition of the subject based on (i) the changes in the pattern of the heart rate variability, (ii) the changes in the glucose level of the interstitial fluid, and (iii) a pattern recognition model trained using prior heart rhythm measurements of the subject and prior glucose level measurements of the subject.

* * * * *